United States Patent
Saad et al.

(10) Patent No.: US 10,166,006 B2
(45) Date of Patent: Jan. 1, 2019

(54) ULTRASOUND SYSTEM WITH DYNAMICALLY AUTOMATED DOPPLER FLOW SETTINGS AS A SAMPLE VOLUME IS MOVED

(75) Inventors: Ashraf Saad, San Diego, CA (US); Thanasis Loupas, Athens (GR); David Hull, Mukilteo, WA (US); Steven John Hill, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 542 days.

(21) Appl. No.: 14/343,488

(22) PCT Filed: Sep. 14, 2012

(86) PCT No.: PCT/IB2012/054812
§ 371 (c)(1),
(2), (4) Date: Mar. 7, 2014

(87) PCT Pub. No.: WO2013/046089
PCT Pub. Date: Apr. 4, 2013

(65) Prior Publication Data
US 2014/0213905 A1    Jul. 31, 2014

Related U.S. Application Data

(60) Provisional application No. 61/541,369, filed on Sep. 30, 2011.

(51) Int. Cl.
*A61B 8/06*    (2006.01)
*A61B 8/08*    (2006.01)
(Continued)

(52) U.S. Cl.
CPC ............. *A61B 8/488* (2013.01); *A61B 8/06* (2013.01); *G01S 15/8981* (2013.01);
(Continued)

(58) Field of Classification Search
CPC ............ G01S 15/8981; G01S 15/8984; G01S 15/8988; G01S 7/52066; G01S 7/52073; G01S 7/52071; A61B 8/488; A61B 8/06
(Continued)

(56) References Cited

U.S. PATENT DOCUMENTS

| 6,068,598 | A | 5/2000 | Pan et al. |
| 6,086,539 | A | 7/2000 | Guracar et al. |

(Continued)

FOREIGN PATENT DOCUMENTS

| CN | 1907230 A | 2/2007 |
| CN | 101273904 A | 10/2008 |

(Continued)

*Primary Examiner* — Angela M Hoffa

(57) ABSTRACT

An ultrasound system performs duplex colorflow and spectral Doppler imaging, with the spectral Doppler interrogation performed at a sample volume location shown on the colorflow image. The colorflow image is displayed in a color box overlaid on a co-registered B mode image. A color box position and steering angle processor analyzes the spatial Doppler data and automatically sets the color box angle and location over a blood vessel for optimal Doppler sensitivity and accuracy. The processor may also automatically set the flow angle correction cursor in alignment with the direction of flow. In a preferred embodiment these optimization adjustments are made automatically and continuously as a user pauses at points for Doppler measurements along a length of the blood vessel.

13 Claims, 11 Drawing Sheets

(51) Int. Cl.
*G01S 15/89* (2006.01)
*G01S 7/52* (2006.01)

(52) U.S. Cl.
CPC ....... *G01S 15/8984* (2013.01); *G01S 7/52066* (2013.01); *G01S 7/52071* (2013.01); *G01S 7/52073* (2013.01); *G01S 15/8988* (2013.01)

(58) Field of Classification Search
USPC ........................................................ 600/441
See application file for complete search history.

(56) References Cited

U.S. PATENT DOCUMENTS

| | | | |
|---|---|---|---|
| 6,126,605 | A | 10/2000 | Washburn et al. |
| 6,176,830 | B1 | 1/2001 | Freiburger |
| 6,293,914 | B1* | 9/2001 | Sumanaweera ......... A61B 8/06 600/443 |
| 6,322,509 | B1 | 11/2001 | Pan et al. |
| 6,464,637 | B1 | 10/2002 | Criton et al. |
| 7,223,242 | B2* | 5/2007 | He ......................... A61B 8/488 600/443 |
| 7,798,968 | B2 | 9/2010 | Li |
| 7,815,572 | B2* | 10/2010 | Loupas ..................... A61B 8/06 600/441 |
| 2003/0045797 | A1* | 3/2003 | Christopher ........ G01S 7/52026 600/453 |
| 2008/0101674 | A1* | 5/2008 | Begelman ............ G06K 9/3241 382/130 |
| 2008/0242996 | A1 | 10/2008 | Hall et al. |
| 2014/0221838 | A1* | 8/2014 | Loupas ............... G01S 15/8984 600/454 |
| 2015/0250453 | A1* | 9/2015 | Jago .................... G01S 15/8979 600/456 |

FOREIGN PATENT DOCUMENTS

| | | |
|---|---|---|
| CN | 101461720 A | 6/2009 |
| WO | 9617549 A1 | 6/1996 |
| WO | 0319227 A1 | 3/2003 |

\* cited by examiner

ULTRASOUND SYSTEM WITH DYNAMICALLY AUTOMATED DOPPLER FLOW SETTINGS AS A SAMPLE VOLUME IS MOVED

This application is the U.S. National Phase application under 35 U.S.C. § 371 of International Application No. PCT/IB2012/054812, filed on Sep. 14, 2012, which claims the benefit of U.S. Provisional Application No. 61/541,369, filed on Sep. 30, 2011. These applications are hereby incorporated by reference herein.

This invention relates to ultrasonic diagnostic imaging systems and, in particular, to ultrasound systems with automated Doppler flow settings.

Ultrasound imaging systems are operable in B mode for tissue imaging, and Doppler modes for flow analysis and imaging. Typical Doppler modes include the power Doppler mode used for both tissue motion and flow imaging, color-flow Doppler for qualitative flow imaging, and spectral Doppler for flow quantification. Doppler can be performed in one dimension (M mode and spectral Doppler), two dimensional imaging, and three dimensional imaging.

Current diagnostic ultrasound systems offer a number of acquisition controls for the user to manipulate in order to achieve the optimal image quality to help with the patient diagnosis. During vascular exams, users frequently use the colorflow Doppler imaging mode to assess and diagnose blood vessels. Users frequently manipulate the color box position to center it on a vessel of interest and manipulate the Doppler sample volume to locate it on the vessel sites of interest to acquire a spectral Doppler waveform of a particular location in the body. Users also manipulate the Doppler angle correction control to align the flow direction cursor with the vessel orientation. Proposals have been made to automate the placement of the flow angle cursor over the blood flow of a vessel as shown by U.S. Pat. No. 6,464,637 (Criton et al.), WO 96/17549 (Goujon), U.S. Pat. No. 6,068,598 (Pan et al.), and U.S. Pat. No. 6,176,830 (Freiburger). Freiburger also discusses automatic placement of the Doppler sample volume based upon the detected location of maximum velocity in an image, setting the pulse repetition frequency (PRF) based upon the maximum detected frequency shift, and automatically setting the gain based upon the amplitude of colorflow data. U.S. Pat. No. 6,126,605 (Washburn et al.) automatically adjusts thresholds and data compression for a Doppler image by using histograms and samplings of colorflow data, and U.S. Pat. No. 6,322,509 (Pan et al.) adjusts the Doppler sample volume position and size based on image data of a blood vessel. WO 03/19227 (Christopher et al.) describes automatic settings of spectral Doppler and colorflow Doppler displays based upon both spectral Doppler and colorflow Doppler information.

To obtain consistent velocity measurements for multiple exams of the same patient or to compare measurements of different patients, users try to maintain a fixed Doppler angle, the angle at which the Doppler beams are transmitted in relation to the direction of flow, and there are two approaches to achieving this goal. One approach is to fix the angle correction cursor over the image and heel-toe manipulate the transducer to align the vessel with the angle line. Another approach is to rely on ultrasound systems offering a feature that adjusts the beam steering angle each time the angle correction is changed by the user to achieve a fixed Doppler angle. However the angle correction is still done manually. What is needed is an ultrasound system which automatically adjusts the beam steering angle and the color box in which Doppler interrogation is performed based upon the characteristics of the blood vessels in the image, and to do so automatically whenever the sonographer moves the sample volume to a new location for a spectral Doppler measurement.

In accordance with the principles of the present invention, a diagnostic ultrasound system is described which automates the color box placement, Doppler sample volume placement, angle correction, and beam steering angle using vessel segmentation and flow image analysis. In a preferred embodiment the automation is carried out each time the user indicates a point in a blood vessel for flow analysis, without the need to adjust any user controls. The optimal ultrasound transmit and viewing parameters are determined and set automatically each time the user indicates a new location for diagnosis, eliminating the time consuming and tedious adjustments otherwise necessary for every selection of a new site of interest. Ergonomic-related injuries from repeated control manipulation are reduced, particularly in the scanning of long vessels such as the carotid artery and lower extremity vessels.

Figure 1:
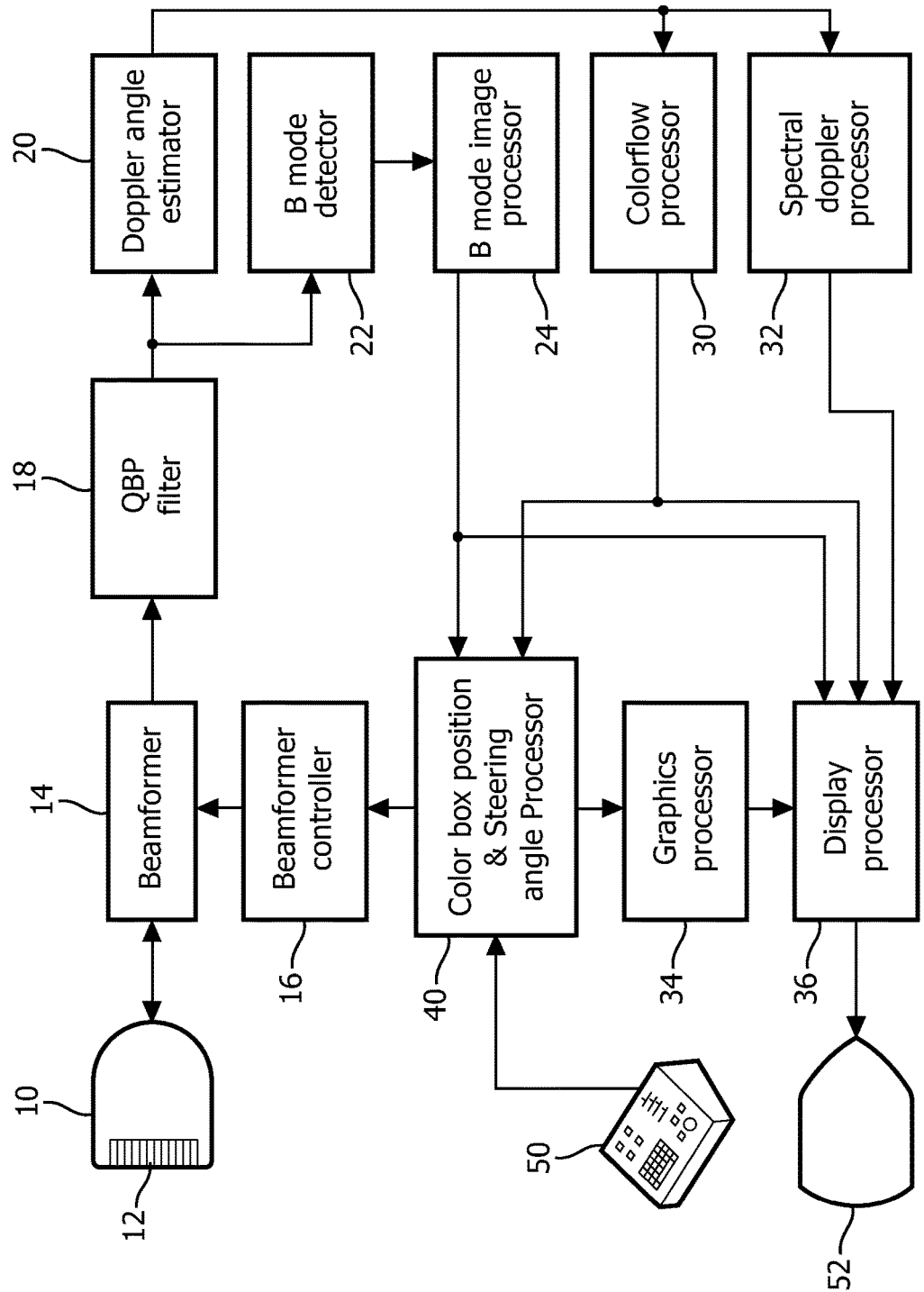
FIG. 1 illustrates in block diagram form a diagnostic ultrasound system constructed in accordance with the principles of the present invention.

Referring first to FIG. 1, an ultrasound system constructed in accordance with the principles of the present invention is shown in block diagram form. An ultrasound probe 10 contains a transducer array 12 of transducer elements which transmit ultrasound waves into the body and receive returning echo signals. The transmitted waves are directed in beams or scanlines to interrogate a region of interest in the body. A one-dimensional array can be used to transmit beams over a single plane for two dimensional imaging, or a two-dimensional array of transducer elements can be used to transmit beams over a volumetric region of the body for three dimensional imaging. The beams can be steered and focused in different directions by the probe to interrogate tissue in specific locations or blood flow in specific directions as explained more fully below. Control and processing of beams on transmit and receive is provided by a beamformer controller 16, which controls a beamformer 14, connected to the elements of the transducer array 12, to transmit properly formed beams and beamform the received signals through delay and summation into coherent echo signals. The beamformer can control the transducer array to scan beams over a desired image plane, for example, and to repetitively scan beams over an area of the image plane in which blood flow is to be assessed at a PRF appropriate for the velocities of blood flow present in that region of the body.

A quadrature bandpass filter 18 processes the echo signal into quadrature I and Q components. The separate components are used by a Doppler angle estimator to estimate the phase or frequency shift of a Doppler signal at points where Doppler interrogation is to be performed. The B mode detector uses the I and Q components to perform B mode detection for tissues images by taking the square root of the sum of the squares of the I and Q components. The detected echo intensities are processed on a spatial basis to form a two or three dimensional image of the tissue in the body, which is processed for display by display processor 36 and displayed on display screen 52.

The Doppler frequencies at locations in the image plane which are produced by the Doppler angle estimator 20 can be mapped directly to velocity values of flow at those locations. This Doppler data is coupled to a colorflow processor 30 which spatially processes the data into a two or three dimensional image format, in which the velocity values are color-coded. This Doppler color map is overlaid over the spatially corresponding B mode image by the display processor 36 to illustrate the locations in the anatomy where flow is taking place and the velocity and direction of that flow by the color coding. Doppler data from a particular point in the image, selected by placement of a sample volume over that location in the image, is coupled to a spectral Doppler processor 32 which produces a spectral display of the variation and distribution of flow velocities at that point with time. The spectral Doppler display is forwarded to the display processor 36 for processing and display of the spectral Doppler display on the display screen 52.

In accordance with the principles of the present invention, colorflow data from the colorflow processor 30 and, preferably, B mode data from the B mode processor 24, is coupled to a color box position and steering angle processor 40. The color box position and steering angle processor controls the automation of settings and features of the colorflow image, including properly positioning the color box, setting the Doppler angle of the Doppler beams, locating the sample volume in the image, and proper positioning of the flow angle cursor. For control of the Doppler angle the color box position and steering angle processor is coupled to the beamformer controller 16 to control the Doppler beam directions. Setup and control of the automation provided by the color box position and steering angle processor is provided by the setting of controls on a user control panel 50. Graphical display of functions controlled by the color box position and steering angle processor, such as the outline of the color box and the flow angle cursor, is provided through a graphics processor 34 which is coupled to the display processor 36 to overlay the graphics over the ultrasound images.

Figure 2:
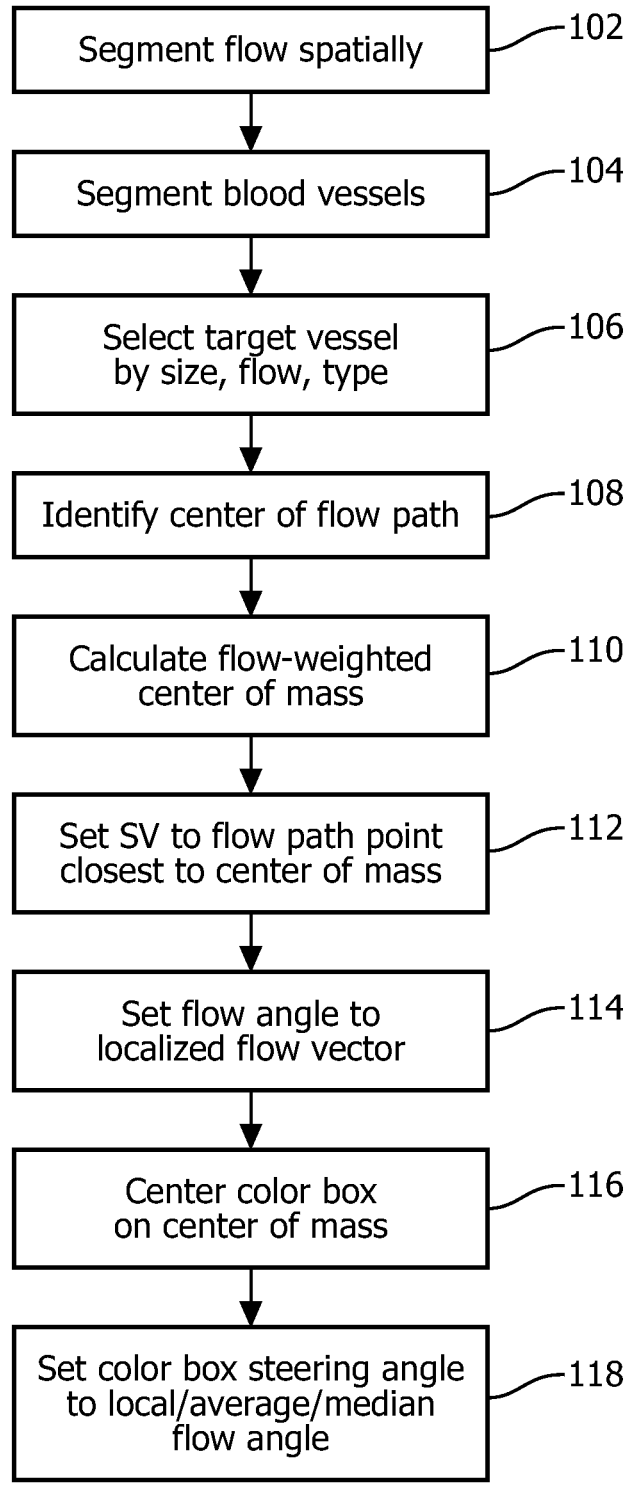
FIG. 2 is a flowchart illustrating the operation of the color box position and steering angle processor of FIG. 1.
Figure 3A:
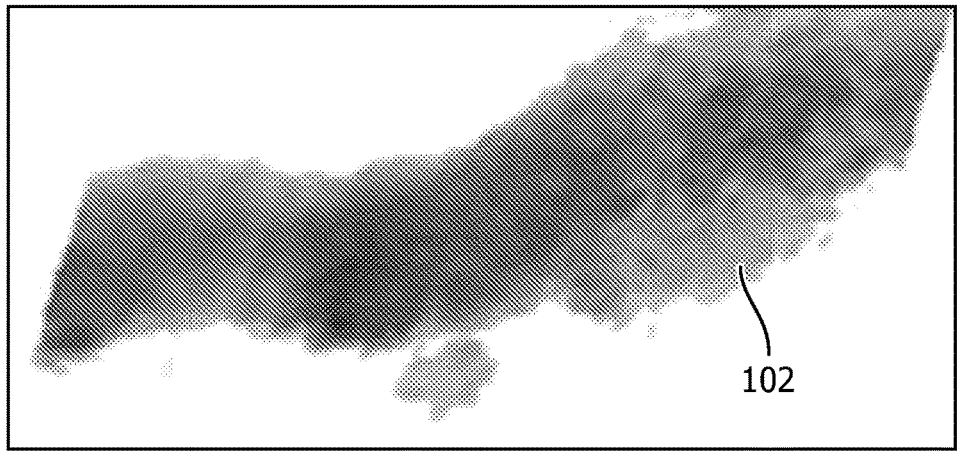
FIGS. 3a and 3b illustrate the segmentation and analysis of a blood flow image of a blood vessel.

The operation of the color box position and steering angle processor 40 is illustrated by the flowchart of FIG. 2. The first step 102 in the process is to segment the flow in an ultrasound image spatially. This may be performed by masking out areas of an image where flow does not occur. In a given implementation the Doppler image from the colorflow processor may provide a spatial image of only the flow locations in the image. This step may also include averaging the flow data over some or all of the heart cycle to produce average or median flow values. In step 104 the blood vessels are segmented, separating them from other motional effects such as perfusion or tissue motion. In step 106 a vessel of interest is selected. A vessel of interest will generally be located in the center of the image acquired by the user. A vessel of interest may also be selected by considering the size, flow, and type of blood vessels which have been segmented. In a carotid exam, for instance, the carotid artery will be identified as an artery and as the largest vessel in the image. FIG. 3a shows an actual ultrasound flow image 120 of the flow in blood vessels which has been segmented and selected for further processing.

Figure 3B:
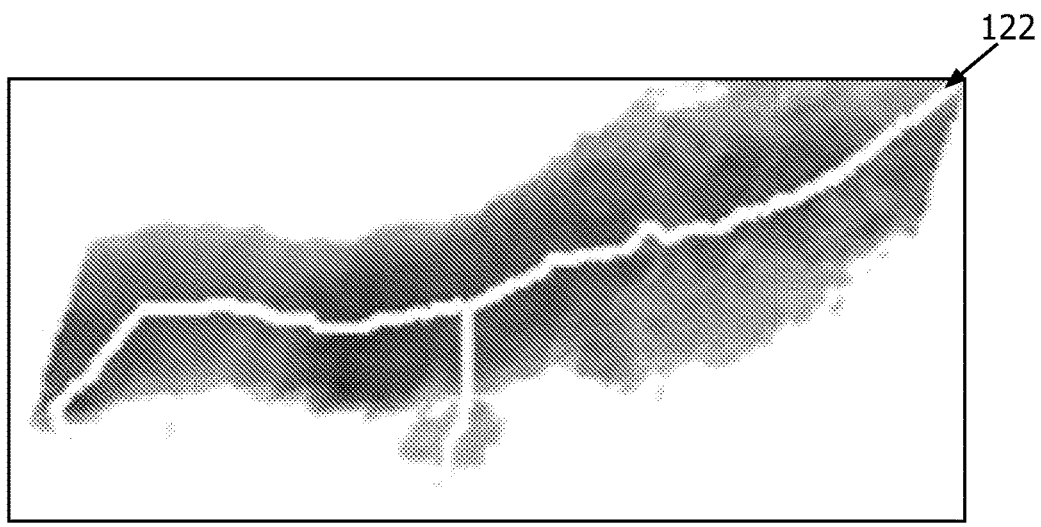

In step 108 the center of the flow path of a vessel is identified. Several techniques for plotting the center of the flow path are known, such as locating the center of the laminar flow field by velocity. Another technique is to analytically draw lines across the blood vessel lumen as shown in the aforementioned Goujon patent application. The centers of the lines or their points of intersection define the center of the vessel. FIG. 3b illustrates the vessel flow of FIG. 3a in which the center of the flow path has been identified by the white tracing 122. This example shows the branching of a connecting vessel at the bottom of the image. In step 110 the flow-weighted center of mass is calculated. This is done by analyzing the spatial dimensions of the flow in the target vessel and finding its center. A simple approach is to measure the length and width of the flow of the vessel and take the center of each. More sophisticated approaches of weighting and integration may also be used.

In a system where the sample volume is to be set automatically, the process next sets the sample volume location in step 112 as the point on the flow path 122 which is closest to the calculated center of mass. This positions the sample volume generally in the center of the image of the blood vessel and in the center of the vessel where flow measurements are generally taken. In step 114 the flow angle is set in accordance with a flow vector localized to the sample volume location. One of the techniques described at the outset of this patent may be used to set the flow angle cursor orientation. Another approach is to set the flow angle cursor to be parallel to the center line 122 as the center line is oriented in the vicinity of the sample volume.

Figure 3C:
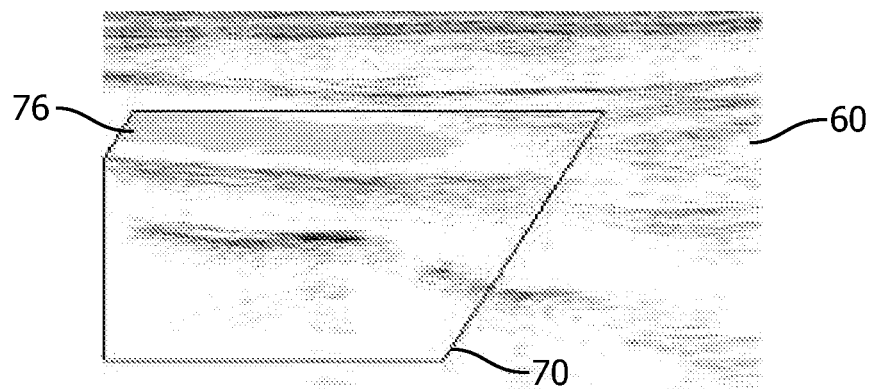
FIGS. 3c and 3d illustrate the automatic repositioning of a color box in accordance with the principles of the present invention.
Figure 3D:
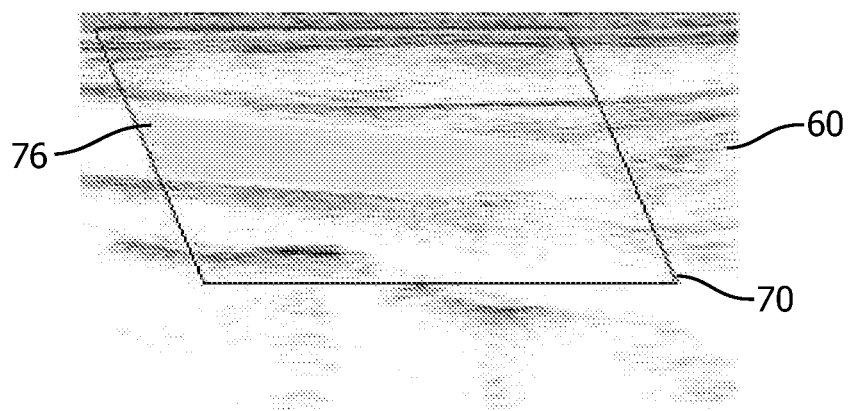

Using the center of mass of the flow previously calculated in step 110, the color box is positioned to be centered about the center of mass. If the center of mass is too close to the side of the image, some of the color box area may be truncated as needed. The color box may also be rescaled in height or width if desired for a uniform appearance. FIGS. 3c and 3d illustrate such a repositioning of a color box 70 in an ultrasound image 60. In FIG. 3c the flow region 76 is the smooth grey region in the blood vessel at the top of the color box 70. The computation of the center of mass of the flow 76 and its repositioning to the center of the color box 70 is shown in FIG. 3d, in which the color box has been relocated so that the flow 76 is more centered in the color box. In step 118 the color box steering angle and the angle of the Doppler beams is set to achieve a desired Doppler angle. For instance if the flow angle set in step 114 shows that the target vessel flow is from the upper left to the lower right in the image, the steering angle will be set to angle from the upper left to the lower right. This steering direction is more nearly in line with the flow direction than a steering angle directed from the upper right to the lower left of the image, which would be more closely orthogonal to the flow direction and hence less sensitive to Doppler flow. A typical steering angle for superficial vessels is ±60°. The setting of step 118 would then set the steering angle to be +60° or −60°, whichever will produce the better Doppler sensitivity. Such a resetting of the color box steering angle is also seen by comparing the color box angle in FIG. 3c with the reset angle in FIG. 3d. This setting of the color box steering angle may be set in accordance with the local flow direction at the sample volume location, or in accordance with average or median flow angles along some or all of the displayed length of the blood vessel. With the color box angle thus reset, the new setting of the angle is coupled to the beamformer controller 16 so that the ultrasound beams transmitted to the color box will be transmitted at the newly determined angle.

Figure 4:
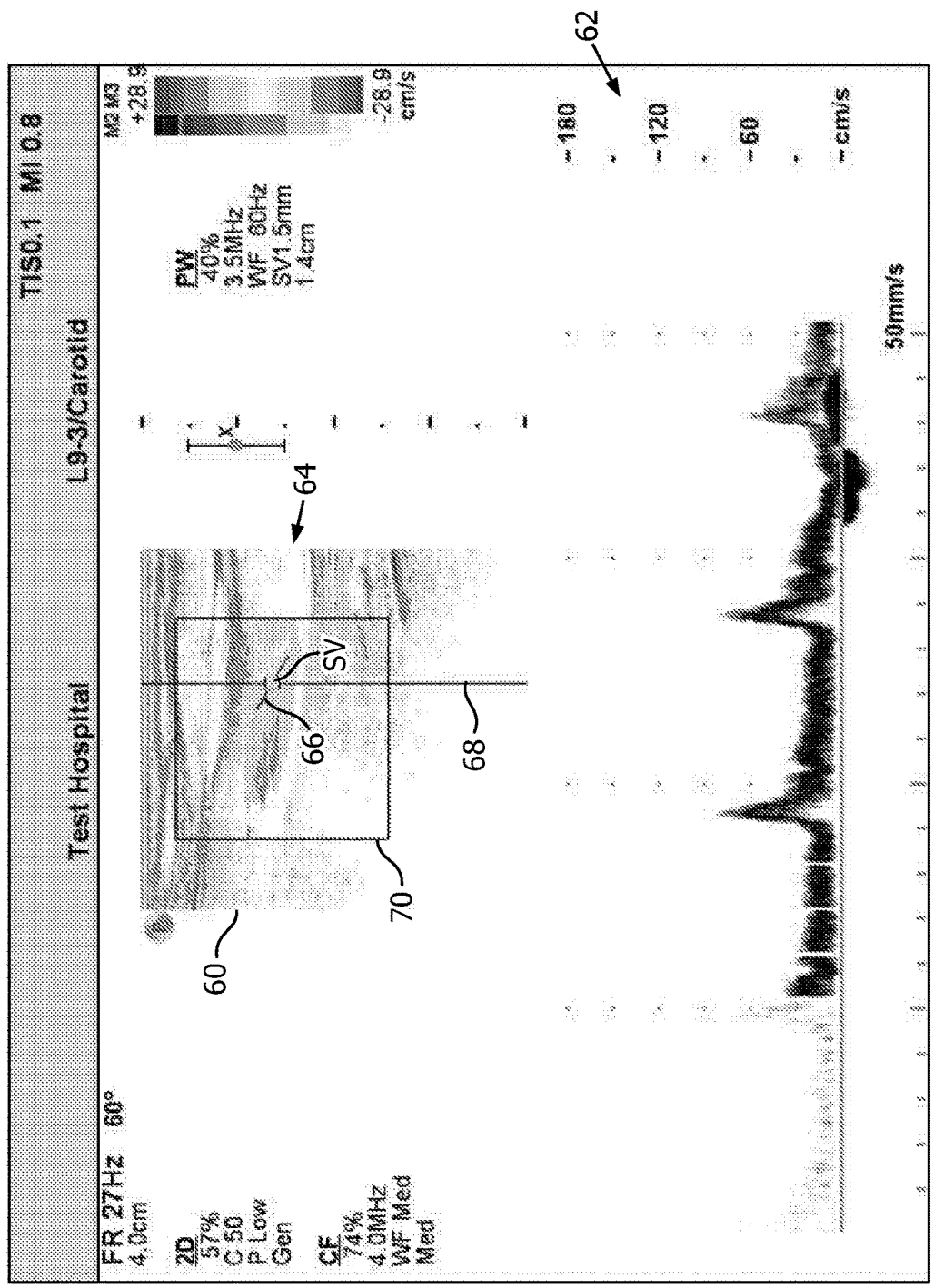
FIGS. 4 to 7 are a sequence of ultrasound system displays illustrating an implementation of the present invention.

The sequence of images of FIGS. 4-7 illustrate an example of how the ultrasound system described above can operate. FIG. 4 shows an ultrasound system display of a typical colorflow/spectral Doppler duplex image with non-optimized Doppler settings. The anatomical ultrasound image 60 is at the top of the screen and the spectral Doppler display 62 is at the bottom of the screen. Doppler interrogation is done inside the color box 70, and a colorflow image is displayed inside this box. Outside the color box 70 the rest of the image is shown in B mode grayscale. The use of a color box delineates the region where Doppler is to be performed, and repeated Doppler transmission for Doppler ensemble acquisition is not performed outside of the color box. Restricting the Doppler transmission to only the color box eliminates the need for repeated line interrogation outside the box and hence limits the total number of transmit-receive cycles needed to produce the image, thereby reducing the time needed to acquire the image which improves the real time frame rate of display. The Doppler beams for the spectral Doppler data are transmitted and received along the beam direction line 68 and the data used for the spectral Doppler display are acquired from echoes returning from the sample volume SV on the beam direction line. The Doppler flow direction cursor 66, used for angle correction, is not aligned with the orientation of the vessel 64 (it should be parallel with the flow direction), and the Doppler steering angle is not optimized for the best color and spectral Doppler sensitivity. In this example the Doppler steering angle is 0°, vertical in the image and normal to the face of the transducer probe.

Figure 5:
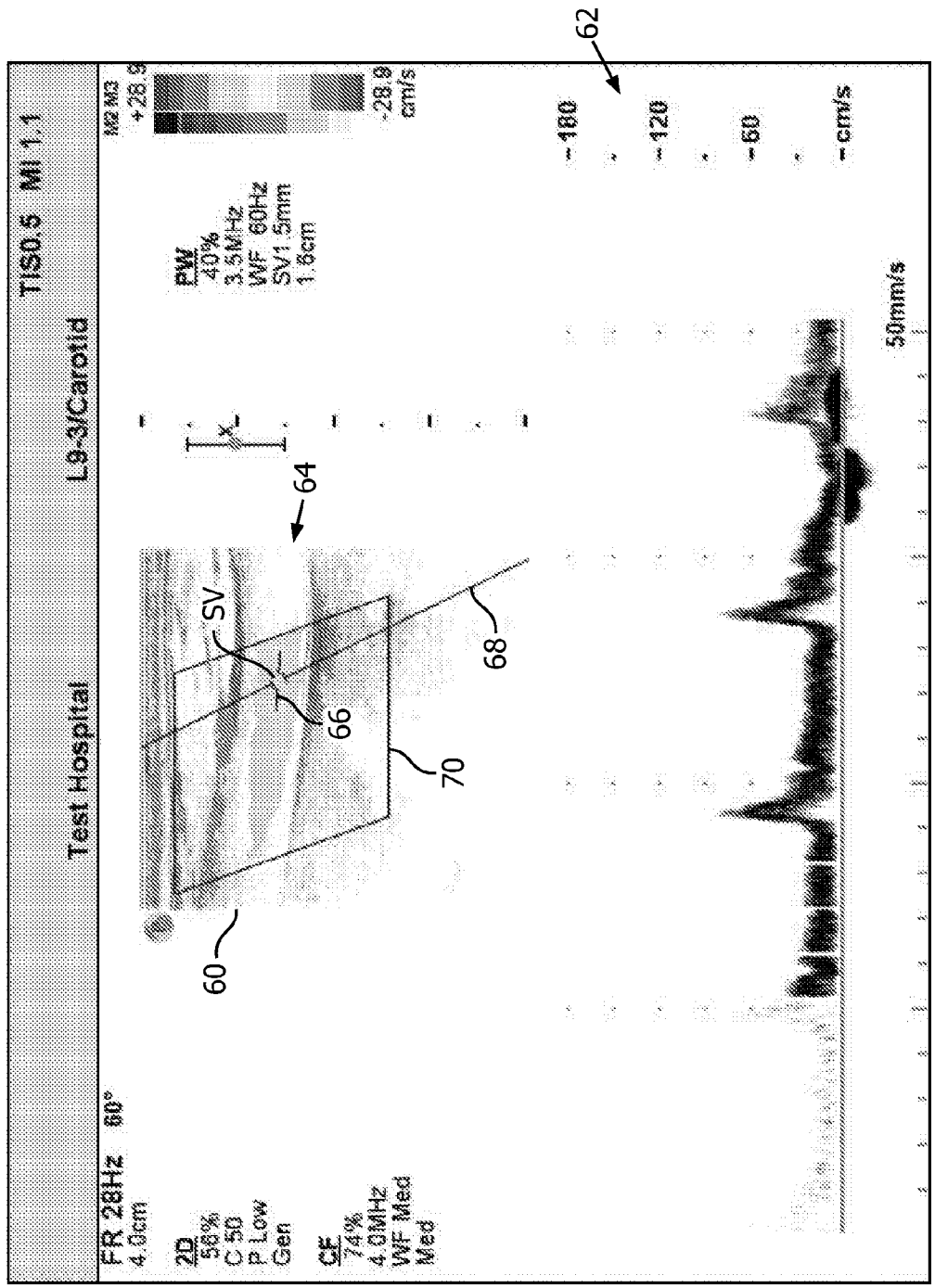

FIG. 5 shows the ultrasound system display after several of the automatic adjustments of the present invention have been made by the color box position and steering angle processor 40. After the user has placed the Doppler sample volume SV on the site of interest in the blood vessel 64, the processor 40 segments the blood flow of vessel 64 and easily identifies vessel 64 (step 106) as the target vessel, the largest vessel in the color box 70. The center of the flow path is identified (step 108) and the orientation of the flow direction cursor 66 is set to be parallel to the flow direction (step 114) as FIG. 5 illustrates. It is also seen that the angle of the color box 70 and beam direction line 68 have been set to achieve a 60° angle with the orientation of vessel 64 (step 118). The new setting will produce better Doppler sensitivity and accuracy due to the more optimal settings.

Figure 6:
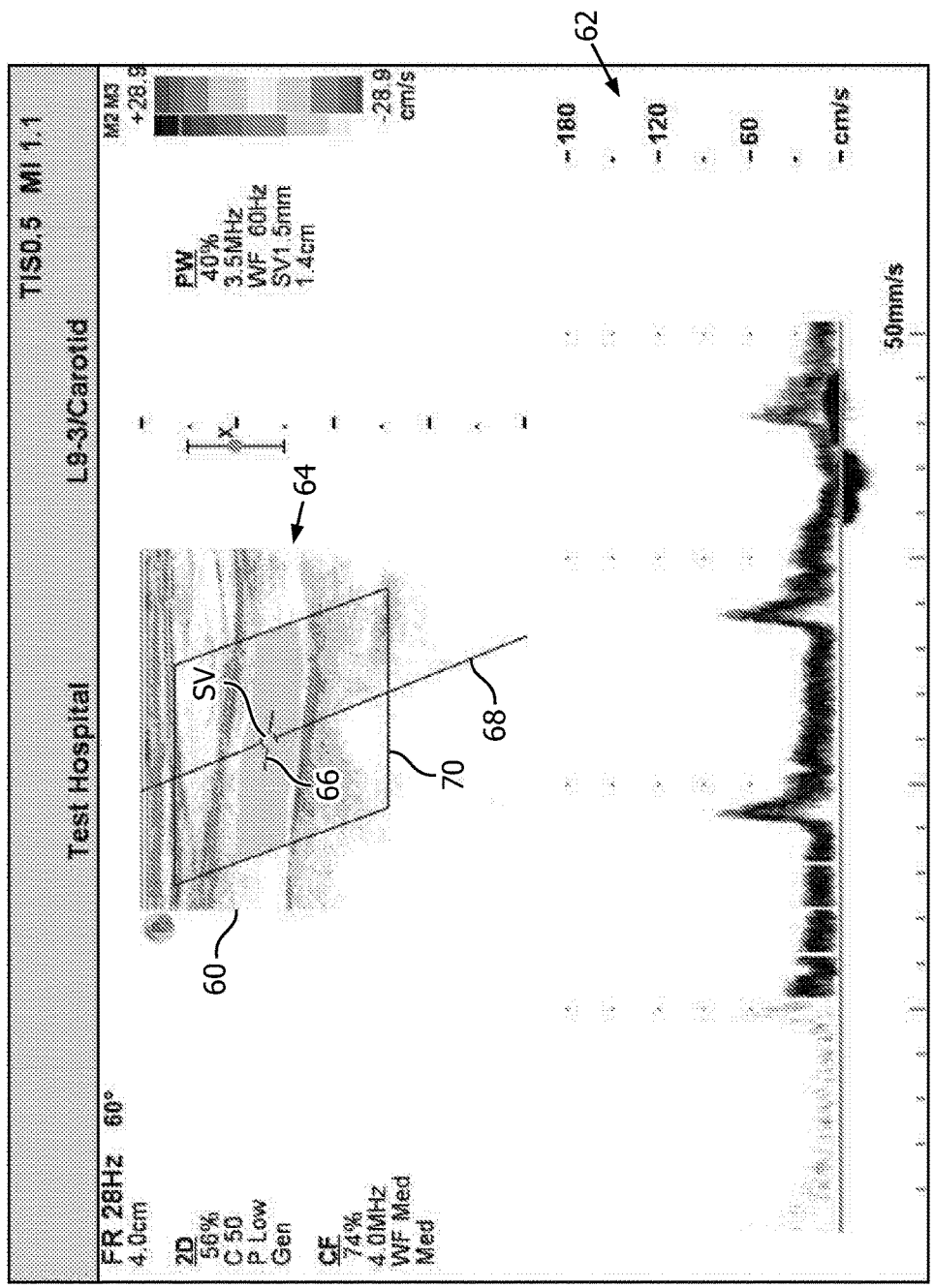

FIG. 6 illustrates a scenario in which the user has moved the sample volume SV to a different location over the blood vessel 64. The automated system has responded by calculating the center of mass of the flow in the vessel 64 inside the color box 70 (step 110). The color box 70 has been repositioned so that the box is centered on the calculated center of mass (step 116); the sample volume SV is in the center of the color box 70. The angles of the flow direction cursor 66 and the beam direction line 68 and color box 70 have also been adjusted to achieve the desired 60° Doppler angle between the beam directions and the flow direction.

Figure 7:
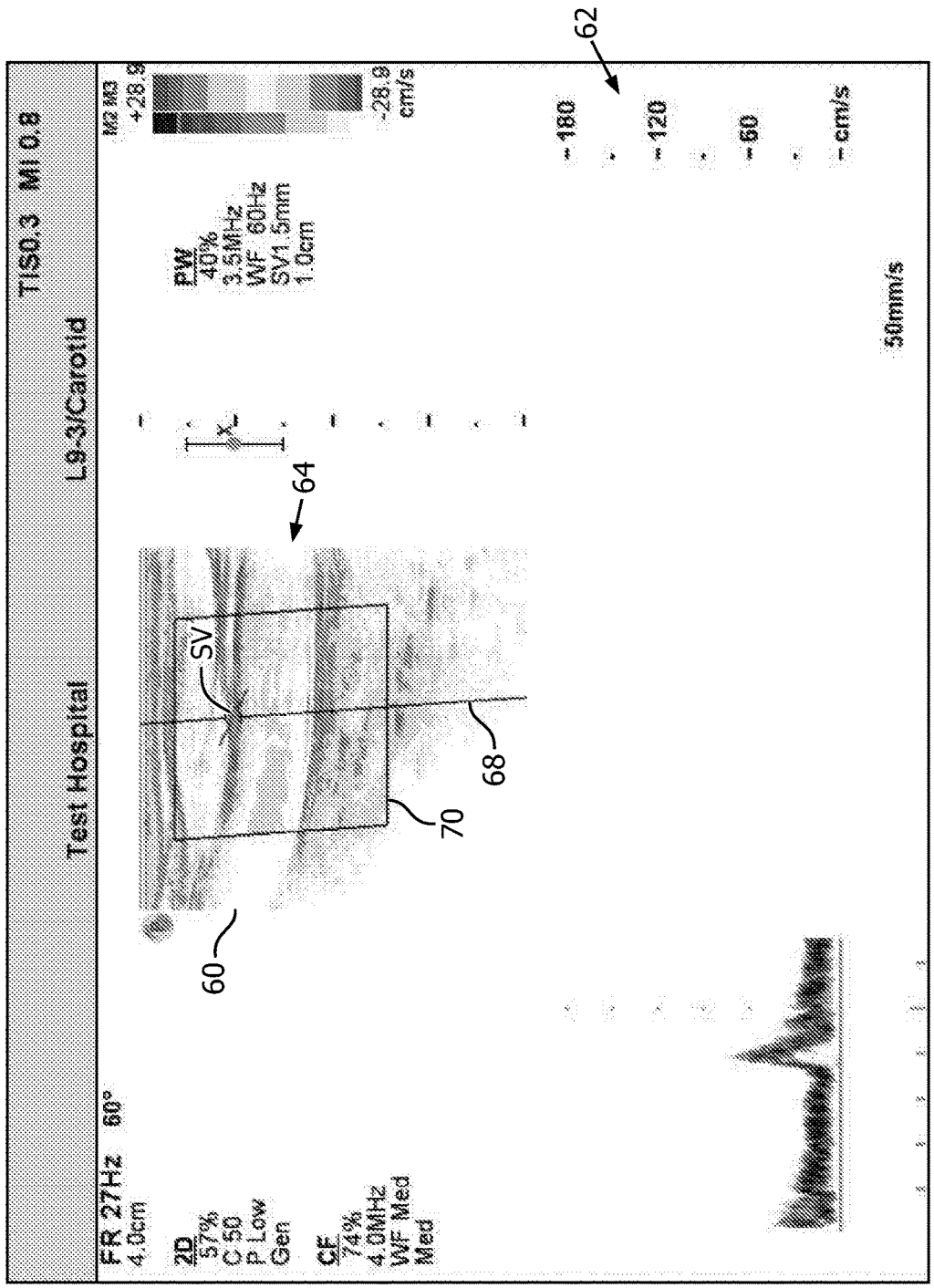

In FIG. 7 the user has changed the image view by moving the ultrasound probe and has repositioned the sample volume SV to a different vessel above vessel 64. The calculations based upon the previously selected vessel 64 and its view now no longer apply to the new site of interest. The calculations of the flowchart of FIG. 2 must now be initialized using new data from the different vessel in order to apply automated adjustments to the different vessel in the new view.

Figure 8:
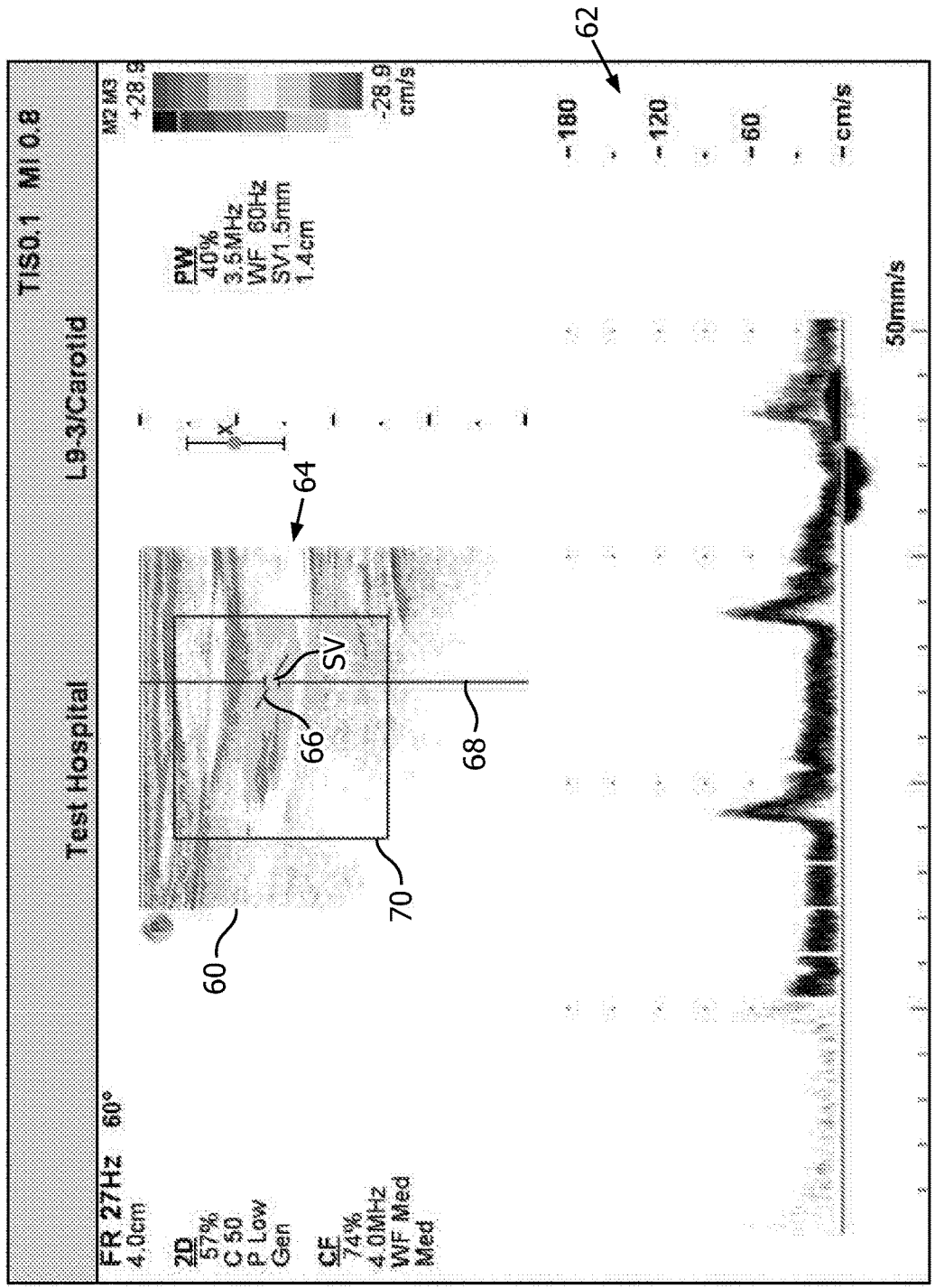
FIG. 8 is an ultrasound system display illustrating controls for automatic flow tracking in accordance with the principles of the present invention.

FIG. 8 illustrates an implementation of the present invention in which the user controls for automated flow adjustment are implemented as softkeys on the display screen and are selected and actuated through a mouse or trackball control on the control panel 50. Button 82, the AutoFlow On/Off button, is actuated to turn the flow automation on or off. Clicking this button will toggle the automated system off (if on) or on (if off). The AutoFlow Reset button 84 will reset the automation results if the user is dissatisfied with them. Actuating this button will cancel all previous calculations by the processor 40 and start them anew. The AutoFlow Config button 86 opens a menu (not shown) in which the user can select which of the automated adjustment features the user wants to use. The user may want to have the system automatically relocate the color box and the angles of the color box and beam direction, for example, but wants to place the sample volume cursor SV and set the orientation of the flow direction cursor manually. In this case the processor 40 can use the orientation of the manually set flow direction cursor to calculate and set the color box and beam direction steering angles, or use computed average or mean flow angles. Actuation of the AutoFlow SV Track button 88 causes the system to dynamically track the sample volume as it is repositioned and continually makes automated flow adjustments as described below.

Figure 9:
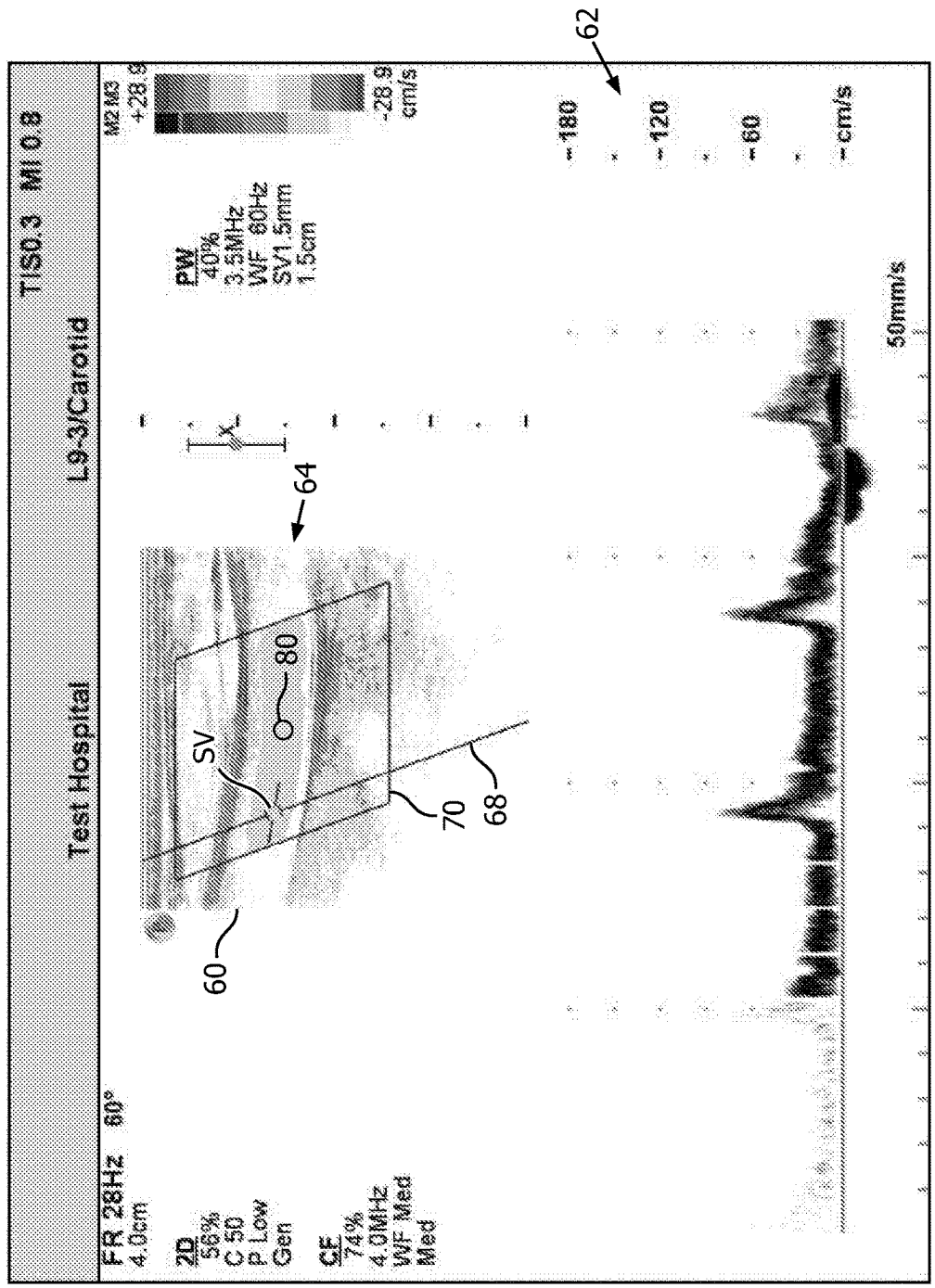
FIGS. 9 and 10 are ultrasound system displays showing automatic tracking of a sample volume, color box placement, and angle correction during an ultrasound exam without user intervention.
Figure 10:
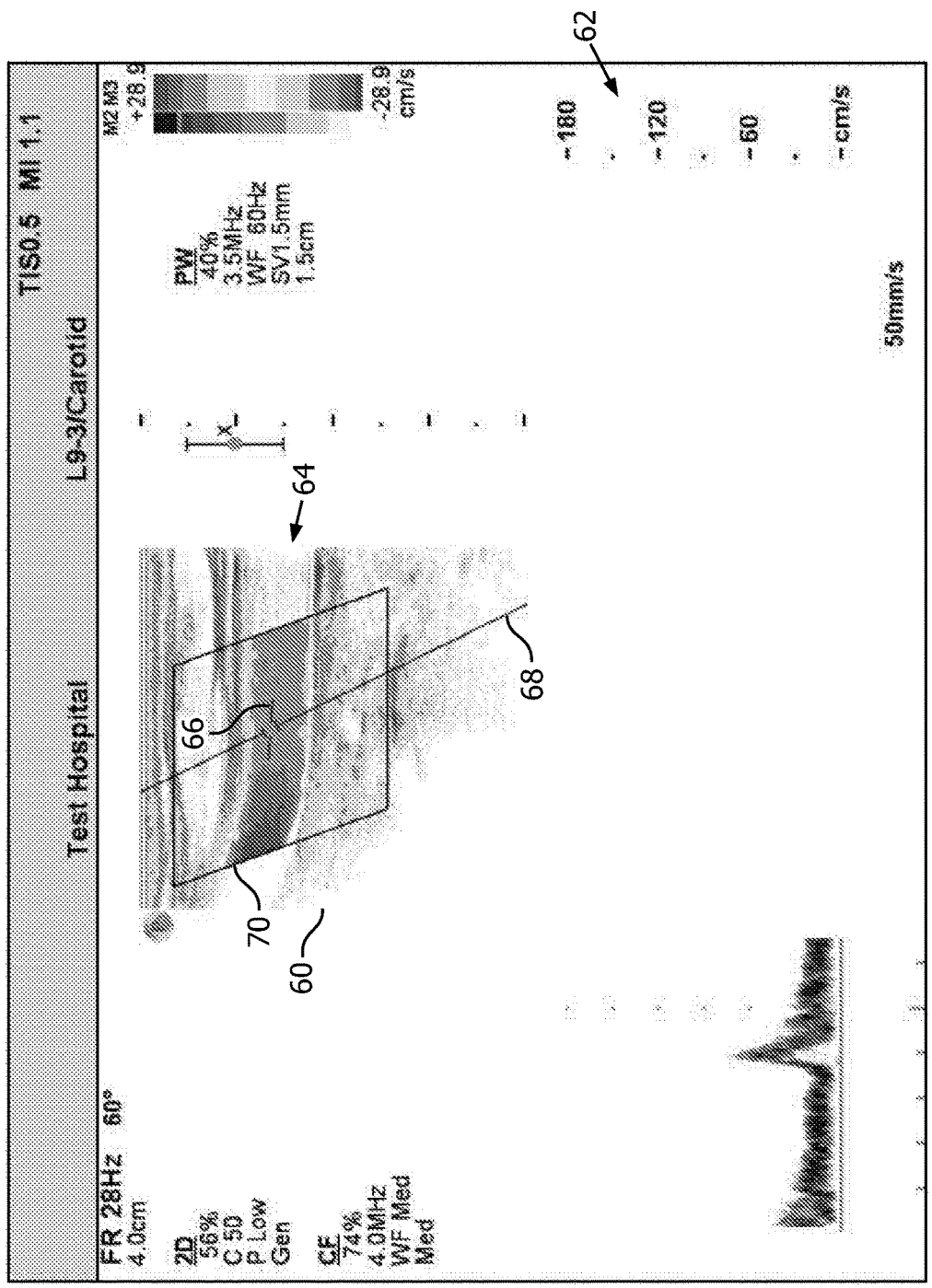

FIG. 9 illustrates a scenario where the user has just taken Doppler measurements at location 80 in blood vessel 64 and wants to take a series of measurements at different points along a section of the blood vessel. In prior art systems, adjustments have to be made to the Doppler acquisition settings for each new measurement, requiring the user to continually make manual adjustments with the controls of the ultrasound system. In this illustration the user is finished with the measurements at location 80 and has moved the sample volume SV to the left to another location in the blood vessel. When the user pauses the sample volume motion to stop at the new measurement location to the left, or clicks on the new location, the ultrasound system immediately makes all of the automated setting adjustments which the user has selected with the AutoFlow Config button settings. The result is illustrated by FIG. 10, where the system has automatically repositioned the color box to be centered around the new sample volume location, has automatically adjusted the Doppler angle of the color box 70 and the spectral beam direction line 68, and has automatically set the angle of the flow direction cursor 66. The system is immediately ready to acquire spectral Doppler data under optimal conditions at the new sample volume location. The exam can continue in this manner. Each time the user moves the sample volume cursor to a new location on the vessel and pauses there, or clicks on the new location, the system will automatically reset the Doppler acquisition controls for optimal data acquisition. The user can take measurements along a continuous length of the blood vessel without the need to manually readjust any of the Doppler control settings, speeding the conduct of the exam and improving the comfort and convenience of the sonographer.

What is claimed is:

1. An ultrasonic diagnostic imaging system for producing a spectral Doppler image of flow for an anatomical location selected from a colorflow Doppler image, the system comprising:

an ultrasonic transducer array probe operable to transmit beams and receives echo signals from a region of a subject where flow is present;

a beamformer operable to control directions in which beams are transmitted by the probe;

a Doppler processor responsive to the echo signals and configured to determine Doppler signals to produce the colorflow Doppler image and the spectral Doppler image;

a display operable to concurrently display the colorflow Doppler image and spectral Doppler image;

a user control which is adapted to be manipulated by a user to indicate the anatomical location where spectral Doppler measurements are taken in a blood vessel shown in a color box that represents a boundary of the colorflow Doppler image; and a color box position and steering angle processor configured to use Doppler signals from the indicated anatomical location to automatically position the color box based on a flow-weighted center of mass for the blood vessel shown in the color box and automatically change a color box steering angle based on a flow vector at the indicated anatomical location, wherein the color box steering angle is represented by a shape of the color box and an angle of the beams transmitted by the probe with respect to the flow vector at the indicated anatomical location;

wherein the color box position and steering angle processor is configured to automatically:

calculate the flow-weighted center of mass for the blood vessel shown in the color box by analyzing spatial dimensions of the flow in the blood vessel and finding a center of the flow; and calculate the flow vector at the indicated anatomical location.

2. The ultrasonic diagnostic imaging system of claim 1, wherein the user control is further operable to move a sample volume cursor on the colorflow Doppler image to indicate the anatomical location; and wherein the user control is operable to cause the color box position and steering angle processor to determine an optimal color box location automatically each time the user pauses the movement of the sample volume cursor.

3. The ultrasonic diagnostic imaging system of claim 1, wherein the color box position and steering angle processor is further operable to automatically determine an angle of a Doppler steering angle line that generates optimal sensitivity to the Doppler signals.

4. The ultrasonic diagnostic imaging system of claim 3, wherein the color box position and steering angle processor is coupled to the beamformer to control the angle of Doppler beam transmission to be consistent with the determined Doppler steering angle line.

5. The ultrasonic diagnostic imaging system of claim 1, wherein the color box position and steering angle processor is further operable to automatically set an orientation of a flow direction cursor, wherein internal angles of the color box are set in consideration of the orientation of the flow direction cursor.

6. The ultrasonic diagnostic imaging system of claim 1, further comprising a graphics processor responsive to the color box position and steering angle processor for graphically delineating the location of the color box on an ultrasound image.

7. The ultrasonic diagnostic imaging system of claim 6, wherein the graphics processor is further operable to graphically delineate the locations of a Doppler sample volume graphic and a Doppler steering angle line on an ultrasound image.

8. The ultrasonic diagnostic imaging system of claim 1, further comprising a B mode processor responsive to the echo signals to produce a B mode image, wherein the colorflow Doppler image is displayed in spatial registration with the B mode image in the color box.

9. The ultrasonic diagnostic imaging system of claim 1, wherein the color box position and steering angle processor is further operable to position the color box to be centered about the calculated flow-weighted center of mass of the flow of the blood vessel.

10. The ultrasonic diagnostic imaging system of claim 1, wherein the color box position and steering angle processor is further configured:

to automatically segment the flow in the colorflow Doppler image;

segment the blood vessel in the segmented colorflow Doppler image; and identify a center of a flow path of the blood vessel, wherein the flow-weighted center of mass is calculated from the center of the flow path.

11. The ultrasonic diagnostic imaging system of claim 10, wherein the segment the flow in the colorflow Doppler image is based, at least in part, by masking areas of the colorflow Doppler image where the flow does not occur.

12. The ultrasound diagnostic imaging system of claim 10, wherein the center of a flow path of the blood vessel is identified, based at least in part on a center of a laminar flow field by velocity in the blood vessel.

13. The ultrasonic diagnostic imaging system of claim 1, wherein the color box position and steering angle processor is further configured to automatically average the flow over some or all of a heart cycle.

* * * * *